United States Patent [19]

Moser et al.

[11] 3,955,409

[45] May 11, 1976

[54] DEVICE FOR TORSIONAL OSCILLATION TESTING

[75] Inventors: Kurt Moser, Freiburg; Beat Höchli, Bern, both of Switzerland

[73] Assignee: Lonza Ltd., Gampel, Valais, Switzerland

[22] Filed: Dec. 19, 1974

[21] Appl. No.: 534,450

[30] Foreign Application Priority Data

Dec. 21, 1973 Switzerland.................. 17999/73

[52] U.S. Cl................................. 73/99; 73/67.3
[51] Int. Cl.².................................... G01N 3/32
[58] Field of Search ............ 73/99, 101, 70.1, 67.3

[56] References Cited
UNITED STATES PATENTS

| | | | |
|---|---|---|---|
| 3,313,148 | 4/1967 | Dautreppe et al. ................ | 73/99 |
| 3,696,664 | 10/1972 | Moser................................. | 73/99 |
| 3,718,028 | 2/1973 | Moser et al. ....................... | 73/99 |

*Primary Examiner*—James J. Gill
*Assistant Examiner*—Stephen A. Kreitman
*Attorney, Agent, or Firm*—Toren, McGeady and Stanger

[57] ABSTRACT

A device is described for the torsional testing of test bodies which avoids reference to the zero point of oscillation and, accordingly, is independent of zero point shifts. The device is of the type wherein a torsional pendulum can be made to undergo damped torsional oscillation and has a transducer for producing a potential corresponding to torsional oscillation. The duration of oscillation between two reversal points of the oscillation and also the damping are measured by the use of an electrical circuit including first, second, third and fourth series circuits. Each circuit includes a condenser and half-wave rectifier and the circuits are connected in parallel through switches to a transducer. Each rectifier is connected to an auxiliary circuit which, when a potential arises in the blocking direction of the rectifier, supplies a signal to a control circuit. The control circuit, after causing a damped oscillation of the pendulum, connects the first series circuit to the transducer, and after the occurrence of a signal in the auxiliary circuit of one of the series circuits, connects the next series circuit to the transducer. A gate opens and closes upon the occurrence of the two signals to pass pulses from a time pulse emitter to an impulse counter. The charging potentials of the condensers are used by a calculation means to determine the damping factor.

7 Claims, 3 Drawing Figures

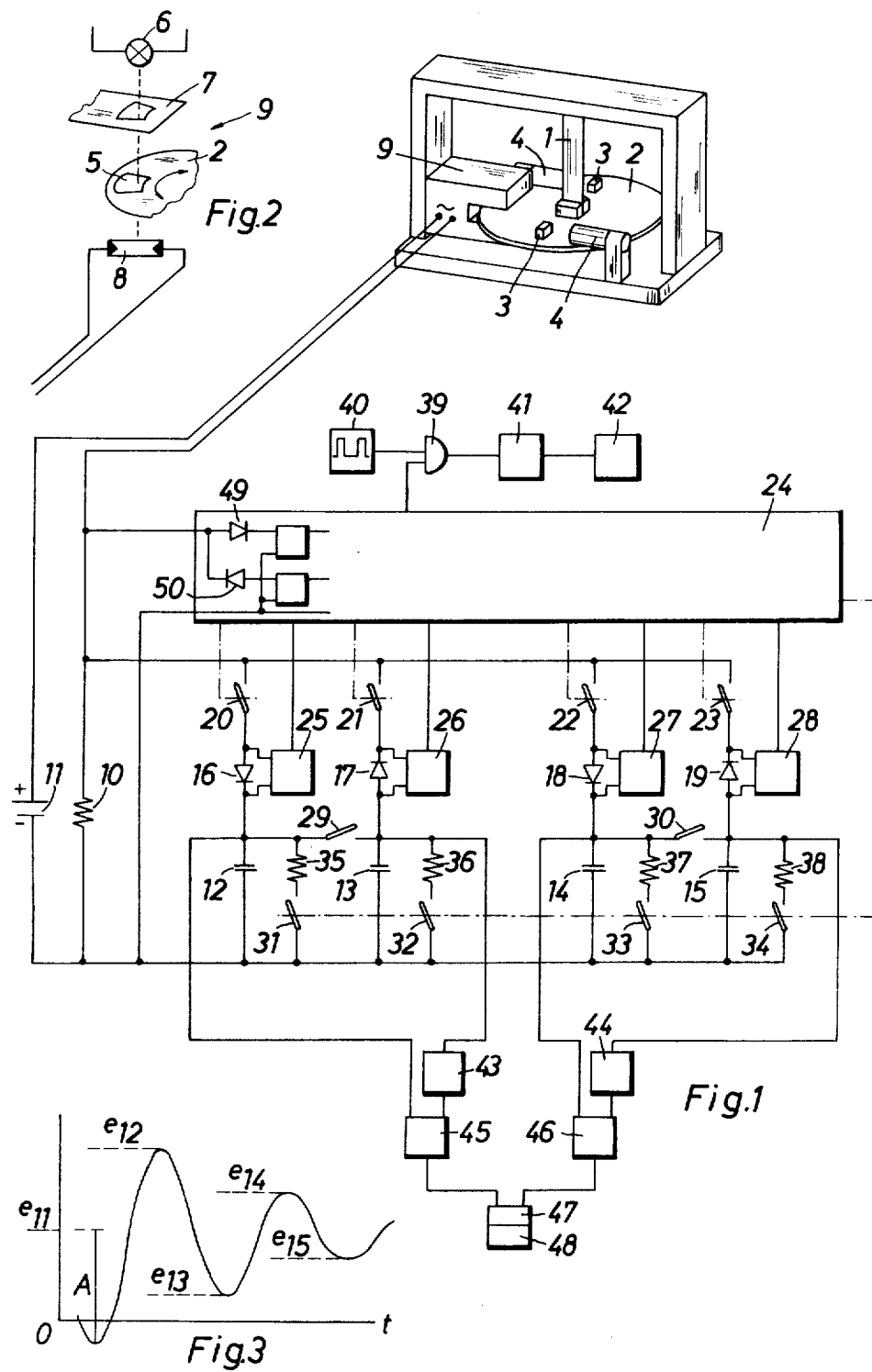

DEVICE FOR TORSIONAL OSCILLATION TESTING

This invention relates to a device for the torsional oscillation testing of test bodies, especially of plastic test bodies, with a device wherein a torsion pendulum with the test body can be made to undergo damped torsional oscillations, a transducer for producing a potential corresponding to the torsion oscillation, means connected to the transducer to measure the duration of oscillation and means for measuring the damping with peak-values stores, which are connected to the transducer by a switch controlled by the oscillation.

Devices of this type are used to determine the modulus of shear and the damping (internal friction) of the plastic. The period of oscillation of the torsion pendulum, the moment of inertia of the oscillation body thereof and the dimension of the test piece are used for calculating the modulus of shear, preferably by a calculator connected to the means for measuring the period of oscillation. The amplitudes, stored in the peak-value stores, of the potential supplied from the transducer are used for calculating the damping, preferably by a calculator connected to the peak-value store.

One difficulty in carrying out torsional oscillation tests of this type, especially with plastic testing, has been that during tests carried out over a wider range of temperature the test body gradually rotates (twists), so that the zero point of the oscillation slowly shifts by an amount which is not negligible in relation to the oscillation amplitudes used, and may even be greater than these. This shift in the zero point leads to the measurement errors if the duration of oscillation is determined by measuring the time between two passages through zero of the oscillation. This is the general practice in the oscillation measurement field, since zero passages are more sharply defined than the oscillation reversal points.

This type of shift in zero point also leads to measuring errors if the damping is determined by measuring two amplitudes. In the graphical evaluation of oscillograms it is known to determine damping without reference to the zero point, in that the total of the absolute values of the positive and negative amplitudes of an oscillation are divided by the corresponding total for the next oscillation (the journal "Kunststoffe" Vol 57, 1967, No. 4, page 258). This method was not however used for the amplitudes stored in peak-value stores.

A device for torsional oscillation testing is known (Swiss Pat. No. 514,138) wherein the member holding the end of the test body which does not participate in the torsional oscillation or the member of the transducer which does not participate in the pendulum motion are pivotally disposed about the pendulum axis by a setting motor, and the output of the transducer is connected to the actual-value input of the control amplifier, supplying the setting motor, of a control device whose nominal value input size corresponds to a specific mutual setting, lying within the operating range of the transducer, of the pendulum oscillation body and of the part of the transducer not taking part in the pendulum oscillations. In this case this part of the transducer is automatically set into a position corresponding to the zero point of the oscillation. This involves considerable constructional costs. This device is also unable to allow for any shift in zero point occurring during an oscillation test.

This invention is based on the problem of avoiding the influence of zero point shifts on measurement of the oscillation duration and of damping by electrical means.

According to the invention this is achieved in that first, second, third and fourth series circuits, each including a condenser and a half-wave rectifier are connected in parallel through switches to the transducer, and the rectifiers in the first and third circuits are polarised oppositely to those of the second and fourth circuits; in that each rectifier is connected to an auxilliary circuit which when a potential arises thereon in the blocking direction of the rectifier supplies a signal to a control circuit, which after causing a damped oscillation of the pendulum connects the first series circuit to the transducer, and after the occurrence of a signal in the auxiliary circuit of one of the series circuits connects the next series circuit to the transducer, and a gate connected between a time pulse emitter and an impulse counter opens on a signal from the auxiliary circuit of the first series circuit and closes on a signal from the auxiliary circuit of a different series circuit; and in that the condensers are connected to a calculator which inverts the charging potential of the condensers of the second and fourth series circuits, and divides the sum of the charging potential of the first condenser and the inverted charging potential of the second condenser by the sum of the charging potential of the third condenser and the inverted charging potential of the fourth condenser to determine the damping factor.

By this device the duration of the oscillation between two reversal points of the oscillation, and also the damping, are measured without any reference to the zero point. Measurement of damping is effected by the principle mentioned above for the graphic evaluation of oscillographs, but completely automatically. The result of the damping measurement is independent of any shift in the zero point, as long as this is less than the smallest amplitude of the pendulum oscillation.

In the course of a large number of oscillation tests over a wide temperature range, especially at high temperature, the total zero point shift can become greater than the minimum amplitude.

A preferred embodiment of the torsional oscillation device provided by the invention avoids the effect of zero point shift even if this is greater than the minimum amplitude. In this embodiment there is disposed between the series circuits and the transducer a direct potential source whose potential is greater than the maximum potential amplitude of the electrical oscillation which charges the condensers; the rectifiers of the first and third series circuits polarised in accordance with the direct potential; the poles of the condensers in the first and second series condensers connected to the corresponding rectifiers are connected by a first switch, and the corresponding poles of the condensers in the third and fourth series circuits are connected together by a second switch; and the control circuit opens the first switch on receiving a signal from the auxiliary circuit of the first series circuit, and the second switch on receiving a signal from the auxiliary circuit of the third series circuit.

Further advantageous constructional details of the device provided by the invention may be seen from the following description of one embodiment in relation to the drawings. In these:

FIG. 1 is a simplified lay-out of a device for torsional oscillation testing.

FIG. 2 is an exploded view of a detail in FIG. 1,

FIG. 3 is an oscillogram.

The device shown includes a torsion pendulum comprising a strip-shaped plastic test-body 1 from which is suspended an oscillation body 2 in the form of a circular horizontal disc.

The oscillation body 2 has two diametrically opposite armatures 3 each disposed at a distance from an electro-magnet 4. As seen from FIG. 2, the oscillation body 2 has at its edge an aperture 5. A light source 6, e.g., a luminescent diode, illuminates a photo-resistance 8 through a fixed aperture 7 and the aperture 5. When the oscillation body 2 is in rest position the apertures half overlap each other provided the oscillation zero point has not shifted. The members 5, 6, 7 and 8 from a transducer 9 (FIG. 1) lying in series with a resistance 10 in the circuit of a DC source 11. The potential of this is large enough to ensure the potential at resistance 10 does not become negative, ie retains the same polarity as current source 11, even for the maximum amplitude of the oscillation used for measurement and for the maximum zero point shift being allowed for.

Four series circuits, each comprising a condenser 12–15 and a half-wave rectifier 16–19 are each connected by a switch 20–23 to the series circuit consisting of current source 11 and the transducer 9. The switches 2-23 are actuated by a control circuit 24, as described below in conjunction with the mode of operation of the device. The rectifier 16 and 18 of the first and third series circuits are polarised to match the DC source 11, ie allow current to pass when the switches 20, 22 are closed. The rectifiers 17 and 19 of the second and fourth series circuits are oppositely polarized.

In parallel with each rectifier 16–19 is connected an auxiliary circuit 25–28. Each of these auxiliary circuits supplies a signal to the control circuit 24 if a potential arises at the rectifier in the blocking direction which is equal to a certain comparison potential. This comparison potential is greater than the noise potential.

Of the two switches 29 and 30, the first is connected between the poles of the condensers 12 and 13, each joined to a rectifier 16 or 17, and the second switch 30 between the corresponding poles of condensers 14 and 15. These switches 29 and 30 are actuated by the control circuit, as described below. Each condenser 12–15 is bridged by a discharge resistance 35–38 in series with a switch 31–34. These switches 31–34 are also controlled by the circuit 24.

An AND gate 39 controlled by the circuit 24 lies between a time pulse generator 40 and a counter 41, followed by a calculator 42 which calculates the modulus of shear from the duration of oscillation.

The condenser 13 is connected to the input of an inverter 43, and the condenser 15 to the input of an inverter 44. Each inverter 43, 44 delivers at its output a potential of the same value but of the opposite polarity to its input potential. The potential at condenser 12 and the potential at condenser 13, inverted in inverter 43, are each fed to one of the two inputs of an adding device 45. The potential at condenser 14 and the potential at condenser 15, inverted in inverter 44, are similarly fed to an adding device 46. The outputs from adding device 45 and 46 are connected to the inputs of a dividing device 47 which supplies a potential corresponding to the damping factor. A logarithmic unit 48 calculates the damping decrement from this potential.

The mode of operation of the device described is as follows:

In the rest position, all the switches 20–23, 29 and 30 are in the open position as shown, and the AND gate 39 is closed.

The electro-magnets 4 are jointly excited for a brief period. A rotation impulse is thus exerted on the pendulum 1, 2 which is caused to make a damped oscillation. The switches 31–34 are then temporarily closed to discharge the condensers 12–15. The excitement of the electro-magnets 4 and the closing of the switches 31–34, 20 and 29 can be, for instance, effected according to a timed program. A further possibility is described below in association with the rectifiers 49 and 50 which are included in the control circuit 24.

After the closure of the switches 20 and 29 the condensers 12 and 13 start to charge up through the rectifier 16. The charging ends when the alternating potential of transducer 9 has reached its positive maximum. The two condensers 12 and 13 are then charged to the total $e_{12}$ of the potential $e_{11}$ of the current source 11 and of the positive amplitude of the alternating potential of the transducer 9. The rectifier 16 is then blocked, and the auxiliary circuit 25 supplies a signal to the control circuit 24. This signal causes switches 20 and 29 to open and switch 21 to close. Since the alternating potential of the transducer 9 drops during the further progress of the oscillation, the condenser 13 discharges. This discharge ends when the alternating potential has reached its next negative maximum. The condenser 13 is then charged to a potential $e_{13}$ which is equal to the sum of the direct potential of the current source 11 and the negative amplitude of the alternating potential, i.e., is smaller than this direct potential.

The rectifier 17 is then blocked, and the auxiliary circuit 26 supplies a signal to the control circuit 24. This control circuit 24 thus causes switches 21 to open and switches 22 and 30 to close, whereupon the condensers 14 and 15 are charged to a potential $e_{14}$ which corresponds to the total of the potential from the direct current source 11 and the amplitude of the following positive half-wave of the alternating potential of the transducer 9. The condenser 15 is then discharged down to a potential $e_{15}$ which corresponds to the total of the direct potential of the current source 11 and the next negative half-wave of the alternating potential of the transducer 9. The sequence of the events thus corresponds to that for the charging of the condenser 12 and discharging of the condenser 13 as described above.

In order to determine the duration of the oscillation, on receiving an impulse from the auxiliary circuit 25 the control circuit 24 supplies a control potential to open the AND gate 39, and switches this off on receiving an impulse from the auxiliary circuit 27. Thus the counter 41 receives the time impulses from the time pulse generator 40 during the duration of an oscillation. This half oscillation period, the dimensions of the test body 1 and the moment of inertia of the oscillation body 2 are utilised in the calculator 42 to calculate the modulus of shear of the plastic. The dimensions of the test body can either be set as standard dimensions in the calculator 42 or can be made adjustable. As will be seen, for determining the duration of oscillation the time is measured between two maxima ($e_{12}$ and $e_{14}$) of the potential (i.e., two reversal points of the oscillation). This interval is independent of any shift in the zero point of the oscillation.

For determination of the damping, the adding means 45 together with the inverter 43 from the difference between the potentials $e_{12}$ and $e_{13}$ of the condensers 12 and 13. This is the sum of the absolute value of the first positive half-wave and the following negative half-wave of the investigated oscillation. In corresponding manner the adding means 46 together with the inverter 44 form the sum of the absolute value of the second positive halfwave and the following negative half-wave of the oscillation. These sums are independent of the position of the oscillation zero point. Thus the damping decrement formed by dividing these sums and logarithmizing the quotient with the means 47 and 48 is also independent of the position of the oscillation zero point. If the limits with which the zero point shift lies, and the size of the potential of the current source 11 are so chosen that at least one negative half-wave after the oscillation excitation is greater than the current source potential, and at least one complete later oscillation still has amplitudes sufficient for evaluation, the device may be so designed that it itself produces a starting impulse to close the switches 20 and 29. With this construction, the control circuit includes the two rectifiers 49 and 50. The rectifier 49 causes closure of switches 20 and 29, while rectifier 50 causes opening of these switches and temporary closure of switches 31–34. This ensures that condensers 12 and 13 are charged at each positive half-wave, but are discharged at the following negative half-wave, if their amplitude (A in FIG. 3) has a larger value than the potential of the current source 11. As long as this is the case, each start is nullified again by discharge of the condensers 12 and 13, and only when this is no longer the case is the start followed by the processes described above.

The switches 20–23, 29 and 30 may be for instance of the integrated MOSFET type (metal oxide-silicon-field effect transistors). The switches 20–23 could remain closed after the closing operation and only be reopened before the next start; because of the damping of the oscillation $e_{14}$ is lower than $e_{12}$ and $e_{15}$ is greater than $e_{13}$, so that because of the rectifiers 16 and 17 neither later charging of the condenser 12 nor a later further discharge of the condenser 13 are possible. This only applies, however, if no zero point shift comparable with the amplitude reduction occurs during the oscillation. Consequently and in order to prevent any influence from possible interference potentials, it is desirable for the control circuit 24, on receiving a signal from one of the auxiliary circuits 25–28, to open the switch 20, 21, 22 or 23 of the corresponding series circuit, especially since these switches 20–23 must in any case be opened before the next start.

The results of measurement with the described apparatus are independent of zero point shifts as long as the transducer 9 converts without distortion the pendulum oscillation which is being investigated. This is the case with the transducer shown in FIG. 2 so long as the equally sized apertures 5 and 7 neither completely coincide during the oscillation nor leave the photoresistance 8 completely darkened. To compensate for larger zero point shifts the device may additionally be equipped with the device referred to above and known from Swiss Pat. No. 514138, by which for example the transducer may be made to follow up a shift in the oscillation zero point. In such instance this device need only make a coarse compensation for the zero point shift. The device as described above is then used for the remaining fine correction.

What is claimed is:

1. In a device for the torsional oscillation testing of test bodies, especially of plastic test bodies, of the type wherein a torsional pendulum with the test body can be made to undergo damped torsional oscillation, and having a transducer for producing a potential corresponding to the torsional oscillation, means connected to the transducer to measure the duration of oscillation and means for measuring the damping with peak-value stores, which are connected to the transducer by a switch controlled by the oscillation, the improvement comprising:

first, second, third and fourth series circuits, each including a condenser and a half-wave rectifier, said rectifiers in said first and third circuits being polarized oppositely to those of the second and fourth circuits;

first, second, third and fourth switches for coupling the respective series circuit in parallel connection to said transducer;

first, second, third and fourth auxiliary circuits each being coupled to a respective rectifier, each for supplying a signal when a potential arises in the blocking direction of its respective rectifier;

a control circuit, responsive to said signals from said auxiliary circuits, said control circuit causing a damped oscillation of said pendulum and, afterwards, connecting the first series circuit to the transducer, and, after the occurrence of a signal in one of the auxiliary circuits, connects the next series circuit to the transducer;

a time pulse emitter;

an impulse counter;

a gate responsive to said time pulse emitter and coupled to said impulse counter, said gate opening upon the occurrence of a signal from the auxiliary circuit of the first series circuit and closing upon the occurrence of a signal from the auxiliary circuit of a different series circuit; and a calculator, responsive to signals from said condensers in said series circuits, said calculator inverting the charging potential of the condensers of the second and fourth series circuits and dividing the sum of the charging potential of the condenser of the first series circuit and the inverted charging potential of the second condenser by the sum of the charging potential of the condenser of the third series circuit and the inverted charging potential of the fourth condenser to determine the damping factor.

2. A device as in claim 1, including a direct current source disposed between the series circuits and the transducer whose potential is greater than the maximum potential amplitude of the electrical oscillation which charges the condensers; the rectifiers of the first and third series circuits being polarized in accordance with the direct potential; a fifth switch for connecting the terminals of the condensers in the first and second series condensers connected to corresponding rectifiers, and a sixth switch for connecting the corresponding terminals of the condensers in the third and fourth series circuits; and the control circuit opening the fifth switch on receiving a signal from the auxiliary circuit of the first series circuit and the sixth switch on receiving a signal from the auxiliary circuit of the third series circuit.

3. A device as in claim 2, including four discharge resistances and four additional switches, each of the condensers being in parallel with a discharge resistance in series with one additional switch, said additional switches being opened by the control circuit before the closure of the first switch which connects the first series circuit with the transducer.

4. A device as in claim 3, including two additional rectifiers, the transducer in series with the direct current source is connected to an input of the control circuit equipped with said two additional rectifiers; and wherein on application to said input of a potential opposite to the direct current source the control circuit temporarily closes the switches in series with the discharge resistances in order to discharge the condensers, and on application to said input of a potential of the same polarity as the direct current source closes said fifth switch and closes the first switch connecting the first series circuit with the series circuit consisting of the transducer and the direct current source.

5. A device as in claim 2, wherein the transducer comprises a light source, a photo-electric transducer, a first element having an aperture which does not participate in the pendulum oscillations and a second element having an aperture which takes part in the pendulum oscillations, said light source illuminating said photo-electric transducer through said apertures and wherein a resistance is disposed in parallel with the series circuit connecting the photo-electric element with the direct current source.

6. A device as in claim 1, including four discharge resistances and four additional switches, wherein each of the condensers being in parallel with a discharge resistance in series with a switch, and said additional switches being opened by the control circuit before the closure of the first switch which connects the first series circuit with the transducer.

7. A device as in claim 1, wherein each auxiliary circuit is a comparison circuit which produces the signal supplied to the control circuit when the potential arising on its associated rectifier in the blocking direction is equal to a reference potential which is greaer than the noise potential.

* * * * *